United States Patent [19]

Ohashi et al.

[11] Patent Number: 4,650,752
[45] Date of Patent: Mar. 17, 1987

[54] METHOD FOR DETERMINING THE FRESHNESS OF FISH AND MOLLUSKS

[75] Inventors: Minoru Ohashi; Nobuhiko Arakawa; Tomoko Asahara, all of Tokyo; Shuichi Sakamoto, Kamifukuoka, all of Japan

[73] Assignees: Oriental Yeast Co. Ltd.; Oriental Electric Co., Ltd., both of Japan

[21] Appl. No.: 643,053

[22] Filed: Aug. 22, 1984

[30] Foreign Application Priority Data

Aug. 26, 1983 [JP] Japan ................. 58-155027

[51] Int. Cl.[4] .................... C12Q 1/48; C12Q 1/42; C12Q 1/26
[52] U.S. Cl. ........................ 435/15; 426/56; 426/643; 435/21; 435/25
[58] Field of Search .................. 435/6, 10, 15, 21, 25; 426/56, 643, 231

[56] References Cited

U.S. PATENT DOCUMENTS 4,045,296  8/1977  Sternberg ................. 435/25 X
4,247,647  1/1981  Barabino et al. ............ 435/25 X

FOREIGN PATENT DOCUMENTS 146597  9/1982  Japan ..................... 435/25

Primary Examiner—David M. Naff
Attorney, Agent, or Firm—McGlew and Tuttle

[57] ABSTRACT

A rapid, accurate and simple method is disclosed for determining an index of freshness of fish and mollusks. The index of freshness is expressed as the ratio of the combined molar concentration of inosine and hypoxanthine to the total molar concentration of the decomposition products of adenosine triphosphate. Each concentration is determined electrochemically from the amount of hydrogen peroxide produced when a sample extract from fish or mollusks is subjected to the action of certain enzymes. The emzymes used for inosine and hypoxanthine concentration are nucleoside phosphorylase and xanthine oxidase and for the concentration of the decomposition products of adenosine triphosphate are alkaline phosphatase, adenylic acid kinase, AMP deaminase and adenosine deaminase in a crude extract obtained from calf intestine, nucleoside phosphorylase and xanthine oxidase. Sodium azide may be added to the sample extract to inhibit errors in measurement caused by the presence of catalase.

2 Claims, 11 Drawing Figures

METHOD FOR DETERMINING THE FRESHNESS OF FISH AND MOLLUSKS

Background of the Invention

1. Field of the Invention

The fields to which this invention applies include the marine product, food processing, analytical instrument, and analytical reagent industries.

2. Description of the Prior Art

Detailed studies to determine the degree of freshness of fish and mollusks, including shellfish have been conducted by Saito et al. (Bull. Jap. Soc. Sci. Fish., Vol. 24, 749–750 (1959)) and by Uchiyama et al. (ibid., Vol. 36, 177–187, 977–992 (1970)).

Further, Uchiyama et al. proposed a simple method for determining the degree of freshness of fish and mollusks, which method was published as Japanese Patent Publication No. 30519/1973.

The invention of Uchiyama et al. was based on the studies of Saito et al. who found that when fish and mollusks are caught, adenosine triphosphate (ATP), an energy storing substance stored in the muscles thereof, undergoes the following stepwise decomposition processes in fish: ATP →adenosine diphosphate (ADP) →adenosine monophosphate (AMP)→inosinic acid (IMP)→25 inosine (HxR)→hypoxanthine (Hx), and the following stepwise decomposition in mollusks: ATP-→ADP→AMP→ adenosine (AdR)→HxR→Hx. Thus the higher the content of ATP in fish and mollusks, the higher the degree of freshness, and the higher the content of HxR and Hx therein, the lower the degree of freshness. [K. Arai: ibid, Bull. Jap. Soc. Sci. Fish., Vol. 32, 174–179 (1966)); F. E. Stone: J. Food Sci., Vol. 35, 565–567 (1970)]

The method which was used by Saito et al. at that time to determine the above ATP-related compounds used column chromatography. This method took up to 2 to 3 days to fractionate the components therein, and involved complicated procedures with the result that it was not widely used. Thus an advantage of the invention of Uchiyama et al. was to shorten the time required to determine these compounds by the use of enzymes.

The invention of Uchiyama et al. provides a method for determining the degree of freshness of fish by using ultraviolet spectrophotometry. The inventors determined the degree of freshness in accordance with the following formula:

$$\text{Degree of decomposition of } ATP\ (\%) = \frac{B}{A} \times 100$$

where
- A: Absorbance at 250 m$\mu$ indicating the amount of nucleic acid-related compounds in a fish extract by perchloric acid.
- B: Absorbance at 293 m$\mu$ indicating the amount of converted uric acid in a fish extract as described below multiplied by a coefficient depending on the kind of fish.

The solution for B was prepared as follows: A separate fraction of the extract solution was subjected to the action of two enzymes, i.e. nucleoside phosphorylase (NP) and xanthine oxidase (XO) whereby HxR and Hx in the solution were converted via xanthine (X) to uric acid (UA). The coefficient was 0.938 for fish which accumulate HxR and 0.815 for those which accumulate Hx. Perchloric acid (PCA), which is a powerful reagent and consequently needs great care in handling, is particularly useful as a protein denaturing agent upon extraction because it does not interfere with the determination of UV absorption. The above formula of Uchiyama et al. is equivalent to the index of freshness of the present invention, which index is described below. However, this method has the following problems: The procedures for determining A and B differ from each other. As mentioned above, the coefficient varies from fish to fish and the procedures of analysis are very complicated. Further, substances other than ATP-related substances may be included in absorbance A.

SUMMARY OF THE INVENTION

Objects of this invention are to provide a more rapid, accurate, and simple method for determining the degree of freshness of fish and mollusks, including shellfish and, in particular, to greatly shorten the enzymatic reaction time; to provide inexpensive analytical instruments; to provide a method which is capable of determining the index of freshness of fish and mollusks in accordance with a predetermined formula for calculation regardless of the type of fish or mollusk; and to make it possible even to use protein denaturing agents such as trichloroacetic acid, which could not be used in the UV spectrophotometric method because of its UV-absorbing properties.

The present invention provides a method for easily determining the index of freshness i.e., the K value of fish and mollusks, which K value is expressed as follows:

$$K(\%) = \frac{HxR + Hx}{ATP + ADP + AMP + AdR + IMP + HxR + Hx} \times 100 \tag{1}$$

where each compound represents its molar concentration, characterized by electrochemically measuring value $d_1$ from the consumption of dissolved oxygen (DO) or the amount of hydrogen peroxide produced due to the combined action of nucleoside phosphorylase (NP) and xanthine oxidase (XO) upon a sample solution, electrochemically measuring value $d_2$ from the consumption of DO or the amount of hydrogen peroxide produced due to the combined action of crude alkaline phosphatase (Crude AP), NP and XO upon another sample solution and determining the K value according to formula (2) as follows:

$$K(\%) = \frac{d_1}{d_2} \times 100 \tag{2}$$

The values $d_1$ and $d_2$ correspond to the combined concentration of the compounds in the numerator and in the denominator of formula (1), respectively.

The above method of Uchiyama et al. is a method for determining the amount of uric acid formed by an enzymatic reaction in a spectrophotometer, while the method of the present invention determines the amount of ATP-related compounds from the amount of dissolved oxygen consumed during specified enzymatic reaction steps.

The method of the present invention is similar to that of Uchiyama et al. in that two enzymes, i.e., NP and XO, are used to determine HxR and Hx in the numerator of formula (1). However, the method of the present invention is quite different from that of Uchiyama et al. in that it uses an electrochemical sensor instead of a spectrophotometer.

The sensors used in the present invention may include any conventional sensor such as a polarographic oxygen sensor, a galvanic cell oxygen sensor or a polarographic hydrogen peroxide ($H_2O_2$) sensor.

The essence of the method of the present invention lies in the fact that the amounts of oxygen consumed or of hydrogen peroxide formed during the enzymatic reaction steps are determined by use of an electrochemical sensors, based on the reaction process shown in formula (3) as follows:

Two molecules of oxygen are consumed concurrently with $H_2O_2$ being formed while each molecule of HxR or of Hx is oxidized to uric acid. Since the output of the sensor is a current which is proportional to twice the molar concentration of the compounds to be determined, the determination thereof can be made without a standard solution of the compounds. Moreover, this determination is not inhibited by any ultraviolet absorbing substance, or by color or turbidity in the sample solution.

The instrument used in the present invention is smaller, light and easy to handle. It can thus be used on site in a processing plant or other location as well as in a laboratory.

BRIEF DESCRIPTION OF THE DRAWINGS

FIGS. 2, 3, 4, 5(1), 5(2), 6 and 7 are calibration curves for ATP, ADP, AMP, IMP, AdR, HxR and Hx, respectively.

DETAILED DESCRIPTION OF THE PREFERRED EMBODIMENTS

The present invention will now be explained in greater detail with reference to the drawings described above.

Figure 1:
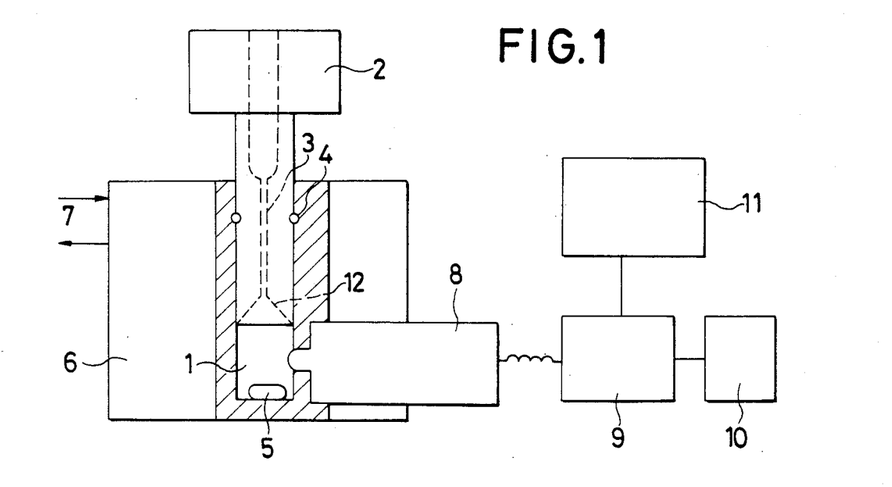
FIG. 1 is a longitudinal cross sectional view of a reaction cell and a flow diagram of the instrument used in the present invention.
Figure 2:
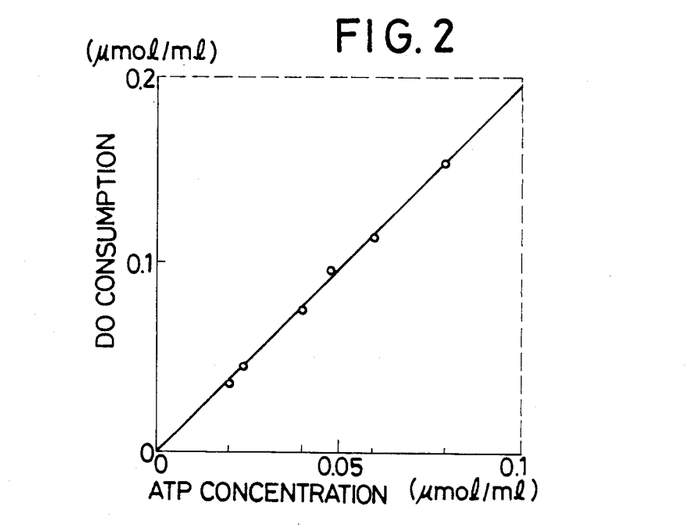
Figure 3:
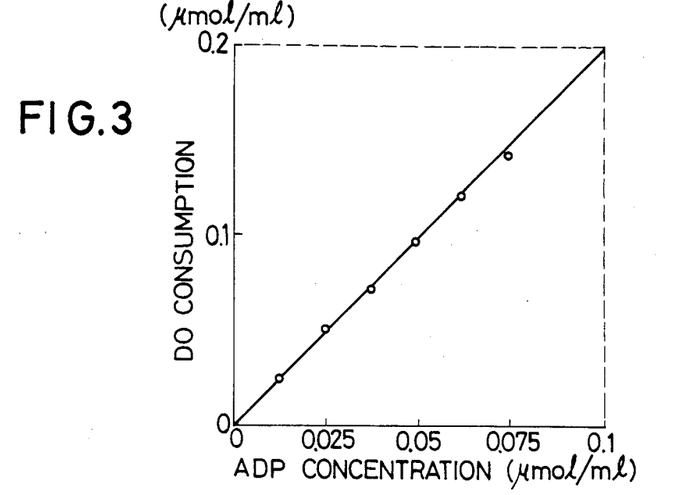
Figure 4:
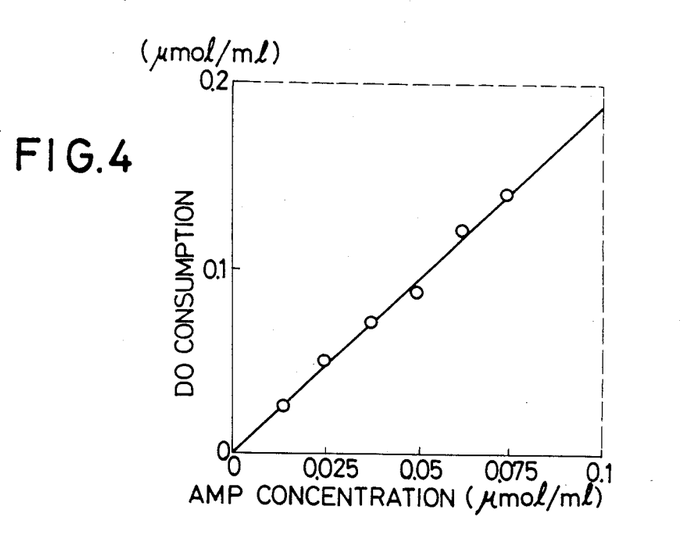
Figure 5:
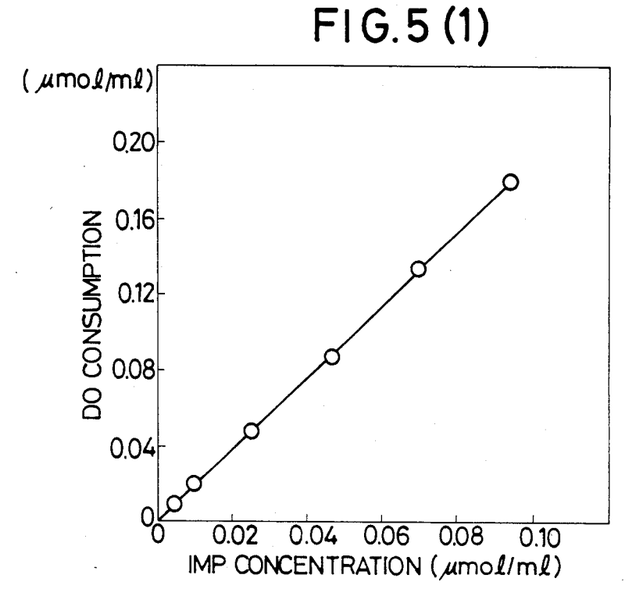
Figure 6:
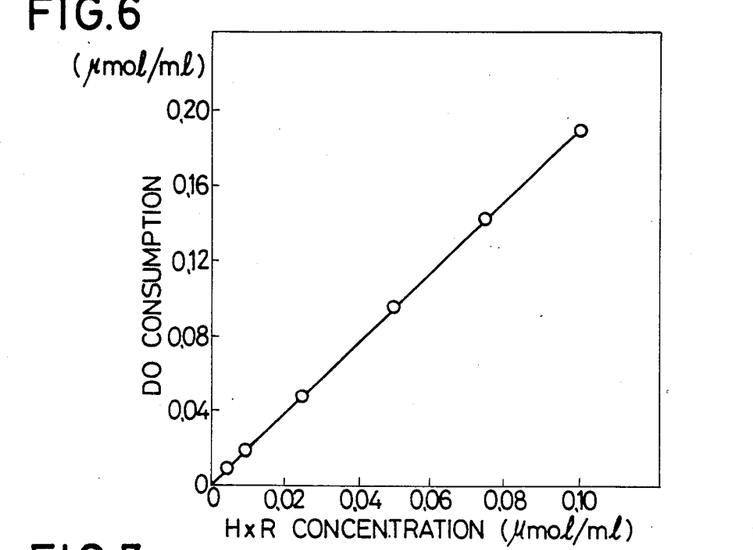
Figure 7:
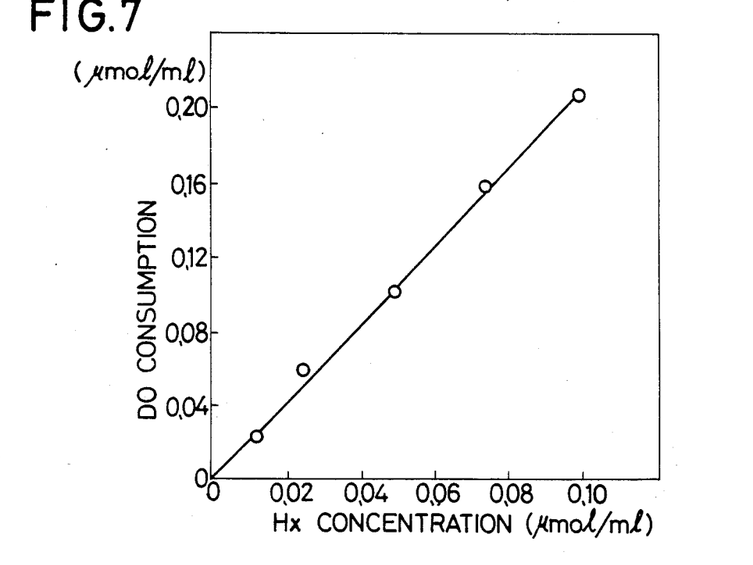

FIG. 1 is a longitudinal cross sectional view of the reaction cell and of the flow diagram of the instrument used in the present invention.

In FIG. 1, 1 is a reaction cell, the volume of which is preferably of from 1 to 2 ml to reduce the amount of enzymes and reagents used. 2 is a stopper in the reaction cell, said stopper being provided with a capillary 3 used for liquid injection in the center thereof, said capillary having, for example, a diameter of about 1 mm. 4 is an o-ring for hermetic sealing (may be omitted), 5 a stirrer bar of a magnetic stirrer, and 6 a jacket for temperature control, through which exterior isothermal water 7 is circulated. The shape of the reaction cell is not specifically limited, but should be so constructed as to be convenient for injection of the reagents, to make possible reaction temperature control and agitation of the reaction mixture for mixing and to prevent oxygen from the outside from being dissolved in the reaction mixture during the agitation thereof. A sensor 8 may be selected from any of the types described above. 9 is an amplifier. A recorder 10 may be any commercially available mV recorder, and preferably should be able to record at a speed of 1 unit per minute with a full range of 10 mV. 11 is a computer.

Figure 8:
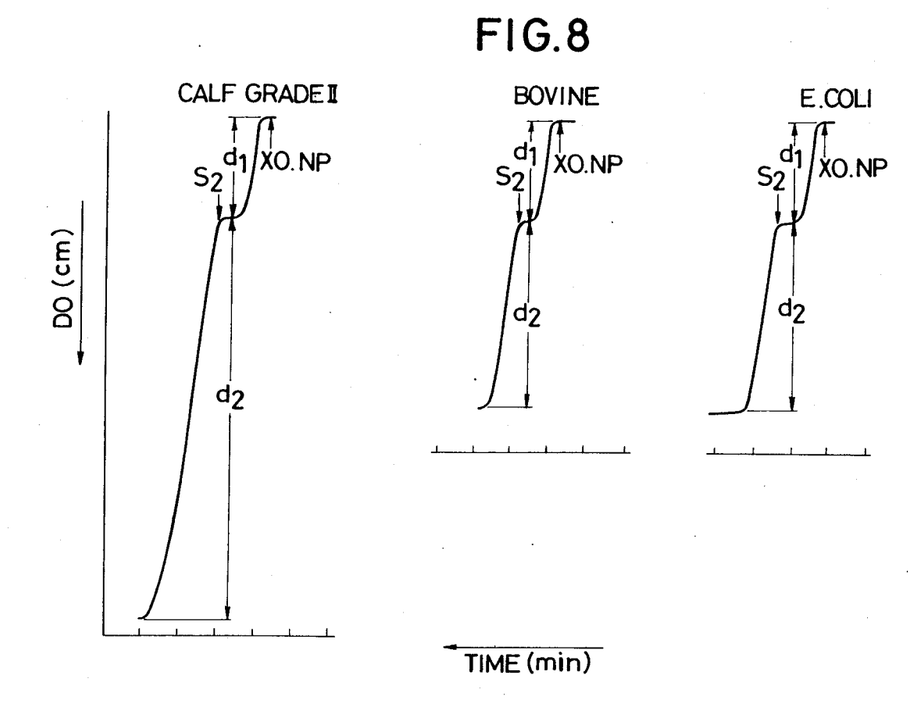
FIG. 8 shows DO consumption curves showing differences in enzymatic activity of AP enzymes extracted from E. coli, bovine intestine and calf intestine.
Figure 9:
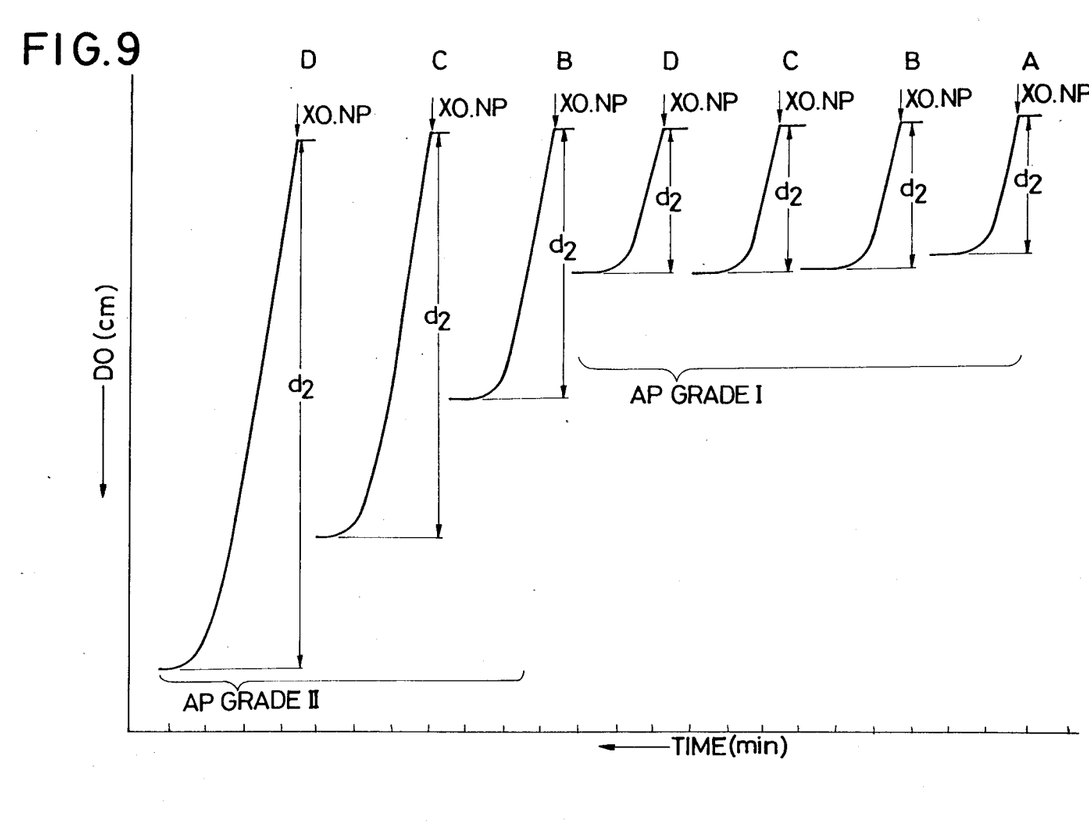
FIG. 9 shows DO consumption curves showing differences in enzymatic activity between a highly purified AP enzyme extracted from calf intestine and a crude AP enzyme.

According to the method of Uchiyama et al., the determination of the compounds in the denominator of formula (1) is made by measuring the UV absorbance at 250 m$\mu$. According to the method of the present invention, for example, the action of a crude alkaline phosphatase (AP) extracted from a calf intestine on a sample solution at a pH of about 10.5 suitable for the enzymatic reaction followed by the action of NP and XO thereon results in the consumption of two molecules of $O_2$ and the formation of two molecules of $H_2O_2$ per molecule of each compound as shown in FIGS. 2–7, with the result that the amounts of each compound may be determined by the converted amounts of $O_2$ or $H_2O_2$. On the other hand, highly purified AP, which acts only to convert IMP to HxR and does not act on ATP, ADP, AMP or AdR can not be used in the present invention. FIGS. 8 and 9 are DO consumption curves clearly showing differences in reactivity between the crude AP enzyme used in the present invention (described as Calf in FIG. 8 and as AP Grade II in FIG. 9) and other AP enzymes. The reagents, enzymes and buffer solutions used in the experiments descirbed above are shown in Tables 1 to 3.

TABLE 1

Standard Reagents

| Reagents | Purity | Manufactuer |
|---|---|---|
| Adenosine-5'-triphosphate (disodium salt) (ATP) | 99% | Oriental Yeast Co., Ltd. |
| Adenosine-5'-diphosphate (disodium salt) (ADP) | 98% | Oriental Yeast Co., Ltd. |
| Adenosine-5'-monophosphate (AMP) | 98% | Oriental Yeast Co., Ltd. |
| 5'-sodium inosinate (IMP) | * | Tokyo Kasei Kogyo K.K. |
| Adenosine (HdR) | 99% | Boehlinger |
| Inosine (HxR) | 99% | " |
| Hypoxanthine (Hx) | 99.5 | Tokyo Kasei Kogyo K.K. |

*1 molecule of inosinate containing 7.5 molecules of water.

TABLE 2

Enzymes Used

| Enzymes | Material for extraction | Manufacturer | Product number | Activity (U/ml) | Activity (U/mg protein) |
|---|---|---|---|---|---|
| Alkaline phosphates (AP), Grade II | calf intestine | Boehlinger | 108154 | 1400 (at 37° C.) | 140 (at 37° C.) |
| Alkaline phosphates (AP), Grade I | calf intestine | " | 567744 | 25000 (at 37° C.) | 2500 (at 37° C.) |
| Alkaline phosphates (AP), Grade I | bovine intestine | Sigma | P-5521 | 900 (at 37° C.) | 1000 (at 37° C.) |
| Alkaline phosphates (AP), Grade I | E. coli | " | P-4377 | 195 (at 37° C.) | 13 (at 37° C.) |
| Nucleoside phosphorylase (NP) | bovine spleen | " | N-3003 | 110 (at 25° C.) | 22 (at 25° C.) |
| Nucleoside phosphorylase (NP) | calf spleen | Boehlinger | 107956 | 100 (at 25° C.) | 20 (at 25° C.) |
| Xanthine oxidase (XO) | cow milk | " | 110434 | 4 (at 25° C.) | 0.4 (at 25° C.) |

Note: All enzymes were used in a liquid state. (AP Grade I was suspended in a sodium chloride solution, while the other enzymes were suspended in an ammonium sulfate solution).

TABLE 3

Buffer Solution

| Uses | Composition | pH | Temperature | Note |
|---|---|---|---|---|
| AP reaction | 1/15 M glycine-NaOH (containing 1 mM Zn & Mg) | 10.5 | 37° C. | |
| XO & NP reaction | 1/15 M phosphate | 7.6 | 37° C. | saturated with air |

TABLE 4

Comparison of AP Reactivity Determination of ATP Decomposition Products unit (μmol/ml)

| | | AP | | |
|---|---|---|---|---|
| Solution to be tested | | Boehlinger calf intestine Grade II | Sigma E. coli | Sigma bovine intestine |
| 1 | Hx 0.25 HxR 0.5 IMP 0.5 Total (1.25) | 1.29 | 1.27 | 1.31 |
| 2 | 1 + AMP 0.5 Total (1.75) | 1.73 | 1.23 | 1.31 |
| 3 | 2 + ADP 0.5 Total (2.25) | 2.09 | 1.34 | 1.40 |
| 4 | 3 + ATP 0.5 Total (2.75) | 2.65 | 1.37 | 1.46 |

TABLE 4-continued

Comparison of AP Reactivity Determination of ATP Decomposition Products unit (μmol/ml)

| | | AP | |
|---|---|---|---|
| Solution to be tested | | Calf intestine Grade I | Calf intestine Grade II |
| A | IMP 0.5 | 0.53 | 0.56 |
| B | IMP 0.5 AMP 0.5 | 0.56 | 1.03 |
| C | B + ADP 0.5 | 0.57 | 1.52 |
| D | C + ATP 0.5 | 0.55 | 2.00 |

As shown in the left column of Table 4-1, a mixed standard solution of Hx, HxR and IMP was prepared as a base solution, to which were added AMP, ADP and ATP to prepared solutions 1 to 4, which were subjected to reactions with specific AP enzymes under the following procedures to determine reactivities with the specific enzymes on the basis of DO consumption curves: TWo AP enzymes, which were different from each other in the degree of purification, were subjected to reaction with solutions A to D described in Table 4-2 above to determine the reactivities thereof. DO consumption curves obtained are shown in FIG. 9. In the figure, the curve for solution A using AP-Grade II is omitted, because the curve was almost the same as that for A using AP-Grade I.

Reaction Conditions:
1. Reaction temperature: 37° C.
2. Volume of reaction cell: 2000 μl
3. Amount of sample solutions:
   Table 4-1:
   $S_1$: 25 μl
   $S_2$: 50 μl ($S_2$ was subjected to AP reaction and diluted twice.)
   Table 4-2:

S₂: 100 μl (This solution was subjected to AP reaction.)
4. G.B. : 180 μl
   AP: 20 μl (28 U)
6. NP: 2 μl (SIGMA) (0.22 u); XO: 10 μl (0.04 u)
7. Reaction procedures:

(a) Table 4-1

200 μl of a sample solution, 180 μl of G.B. and 20 μl (7 U) of AP were mixed in a separate cell to be reacted at 37° C. A reaction time of 30 minutes was fixed in order to determine the reactivity of the enzymes, but a period of several minutes was sufficient for the AP pre-reaction to be completed.

A reaction cell (1 in FIG. 1) filled with an air saturated P.B. was sealed by a stopper 2. A liquid entered into a capillary 3 of the stopper provided a water-sealing effect, i.e., functioned to prevent $O_2$ from entering thereinto from the atmosphere. 250 μl of a sample solution $S_1$ was then injected through the capillary by use of a microsyringe, followed by the injection of 12 μl of a mixed enzyme solution of XO and NP (XO:NP =5:1). Immediately thereafter, DO consumption took place, and DO consumption curves based on HxR +Hx were recorded. After confirming that DO consumption had stopped by monitoring consumption ($d_1$), 50 μl of a sample solution $S_2$ subjected to AP pre-reaction was injected to obtain DO consumption curves based on ATP +ADP +AMP +IMP +HxR +Hx to determine consumption ($d_2$). (See FIG. 8 showing sample solution 4 of Table 4-1). When a sample containing AdR was tested, DO consumption curves based on ATP +ADP +AMP +AdR +HxR +Hx were obtained. In the above consumption $d_2$ reaction, since the pH of the reaction mixture was controlled at approximately the neutral value, the action of AP contained in the sample solution $S_2$ was inhibited, and only XO and NP therein reacted.

(b) Table 4-2

Since neither HxR nor Hx was contained in solutions A to D in Table 4-2, after injecting 100 μl of a sample solution $S_2$ subjected to AP pre-reaction in the same manner as above into the reaction cell, 12 μl of a mixed enzyme solution of XO and NP was injected to determine consumption ($d_2$) as shown in FIG. 9.

To a reaction cell filled with an air-saturated P.B. was injected 100 μl of an 0.5 M $Na_2SO_3$ solution containing a trace amount of cobalt chloride. A consumption curve from DO saturation to DO zero was obtained to determine consumption ($d_0$), which corresponds to the saturated amount of $O_2$, i.e., 0.214 μmol/ml at 37° C.

8. Calculation method:

Concentrations of the compounds to be determined were obtained from $d_1$ and $d_2$ in accordance with formula (4) below. Results are shown in Tables 4-1 and 4-2.

$$C = \frac{d \cdot C_{02} \cdot V}{d_0 \cdot 2 \cdot V_s} \quad (4)$$

In formula (4):
C: concentration of the compound to be determined (μmol/ml)
d: DO consumption (cm) with respect to the compound to be determined
$d_0$: DO consumption (cm) with respect to air-saturated water
$C_{02}$: oxygen concentration in air-saturated water (μmol/ml) It is 0.214 (μmol/ml) at 37° C. number of oxygen equivalents (from the relationship shown in FIGS. 2 to 7)
V: volume (μl) of the reaction cell
$V_s$: volume (μl) of the sample solution ($S_1$ or $S_2$)

As can be seen in Tables 4-1 and 4-2, only in the case where a crude AP (Boehlinger AP Grade II, Lot No. 1272123) was used was a value responding to the total concentration of the compounds obtained. With solutions of other AP enzymes, no values responding to AMP, ADP or ATP were obtained. For confirmation, the use of a crude AP (Lot No. 1231123), different from that mentioned above in Lot No. 1272123, resulted in the same reactivity as above, showing that this reactivity was also a basic characteristic of the crude enzyme. The AP activity of the purified AP (Boehlinger AP Grade I) per mg of protein was 2,500 I.U., while that of the crude AP was only 140 I.U., i.e., 5.6% compared to the former. This shows that enzymatic proteins other than AP remained in the proteins in the crude AP in large amounts. Since adenylic acid kinase (myokinase), AMP deaminase and adenosine deaminase, which participate in the conversion of are presumed to be present in sufficient amounts in the group of enzymes mentioned above, the functions and effects thereof in the present invention can be obtained.

Although the effects described above may also be obtained by a method in which a phosphatase such as myokinase or apyrase combined with deaminases are used to determine ATP, ADP and AMP, the method of the present invention has the advantage that the amounts of each compound can be electrochemically detected and determined by using only crude AP, NP and XO.

Moreover, as is apparent from the DO consumption curves, according to the method of the present invention the detection described above may be performed in about 3 minutes and, in the event that the determination of the K value in formula (1) is required, there is no need to convert the DO consumption to its concentration unit. As a result, the K value may be calculated more simply and rapidly compared with the conventional method using optical density.

Table 5 shows an example of studies of the coefficient of variation (C.V.) of measurements according to the method of the present invention. Measurements were made by using a standard sample solution having a total concentration of 4.5 mM consisting of 1 mM of each of ATP, AMP, IMP and HxR, and 0.5 mM of Hx, using $S_1=10$ μl and $S_2=20$ μl in accordance with the method described above.

The results in Table 5, show that the method of the present invention is sufficiently accurate to practicably determine the K value.

TABLE 5

| | Evaluation of the K value of a Standard Solution | | |
|---|---|---|---|
| | $d_1$ (cm) | $d_2$ (cm) | K value (%) |
| 1 | 2.32 | 7.32 | 31.7 |

TABLE 5-continued

| Evaluation of the K value of a Standard Solution | | | |
|---|---|---|---|
| | $d_1$ (cm) | $d_2$ (cm) | K value (%) |
| 2 | 2.20 | 7.25 | 30.3 |
| 3 | 2.20 | 7.37 | 29.9 |
| 4 | 2.15 | 7.32 | 29.4 |
| 5 | 2.16 | 7.30 | 29.6 |
| 6 | 2.11 | 7.20 | 29.3 |
| 7 | 2.01 | 7.25 | 27.7 |
| 8 | 2.01 | 7.18 | 28.0 |
| 9 | 2.18 | 7.10 | 30.7 |
| 10 | 2.25 | 7.15 | 31.5 |
| Average | 2.16 | 7.24 | 29.8 |
| Standard deviation | 0.097 | 0.086 | 1.319 |

The results obtained show that $d_0=16.81$, that the concentration of HxR + Hx was 1.37 μmol/ml (theoretical value: 15.0 μmol/ml), and that the total concentration was 4.61 μmol/ml (theretical value: 4.50 μmol/ml).

The method of the present invention makes it possible to use trichloroacetic acid (TCA) as shown in the Examples as well as the conventionally used PCA as the protein denaturing agent upon extraction of compounds from a sample. Although the method according to the conventional optical determination principle makes impossible the use of TCA due to its UV absorbing property, the use of TCA is advantageous in that it is safer to handle than PCA that a small amount of KOH as the neutralizing agent can be used and that both labor and time can be saved in the preparation of sample solutions since there is no formation of precipitation in neutralization, while the use of PCA requires filtration because of the formation of precipitation in large amounts.

Although an extract residue may be separated by use of a centrifuge, natural filtration with a coarse filter paper is satisfactory. Sampling by use of a syringe fitted with a filter avoids having to filter.

Figure 10:
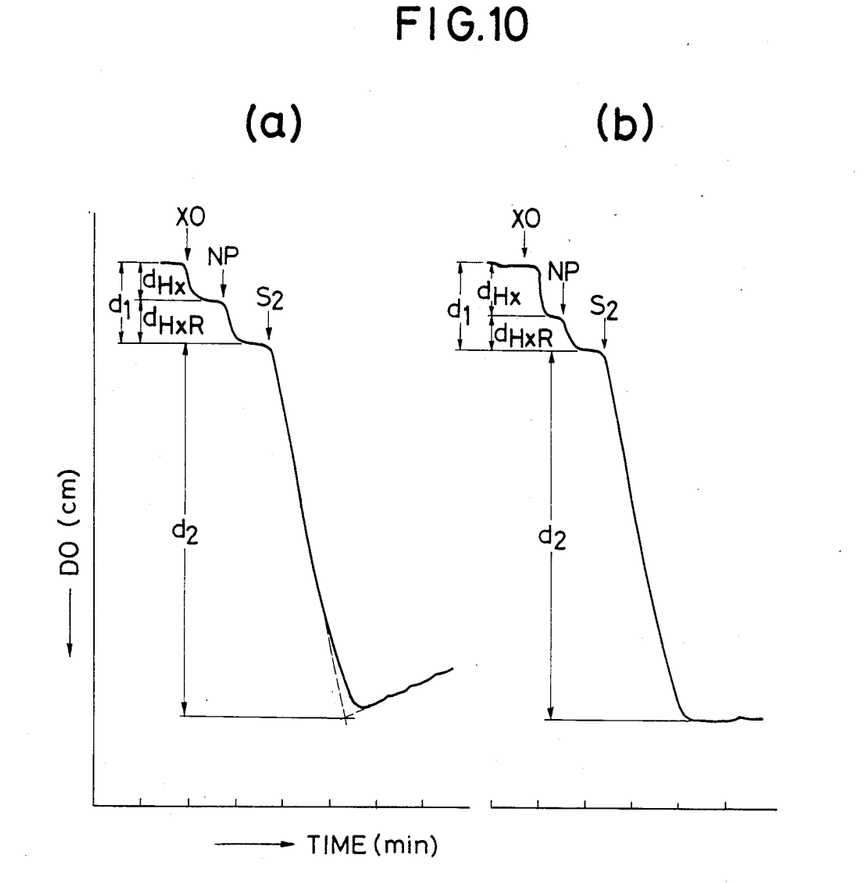
FIG. 10 shows DO consumption curves and the correction of one DO consumption curve distorted by the presence of a catalase.

In the practice of the method of the present invention, a rise in the DO consumption curve (or a fall in the $H_2O_2$ formation curve) may occur to reduce accuracy in measuring $d_1$ and $d_2$ due to the presence of an $H_2O_2$-decomposing catalase in the enzyme or specimen used. Although this reduction in accuracy may be corrected to some extent by extrapolation, it is preferred to inhibit the action of the catalase by adding about 1 μmol/ml of sodium azide ($NaN_3$) to the reaction solution as shown in FIG. 10. A rise in the DO consumption curve due to the presence of catalase is shown in FIG. 10-(a), while FIG. 10-b, using a solution with pre-added sodium azide, shows no rise taking place in the DO consumption curve due to the presence of catalase.

EXAMPLE 1

Determination of the K value of Squid

Sample: A squid packed in ice was used.
Storage Conditions: Refrigerated at 4° C.
Preparation of Sample:
10 g of squid was cut into small pieces and 10 to 15 ml of a 10% TCA solution was added thereto and was ground up for filtration. To the resulting filtrate was added 10 N KOH to neutralize the filtrate by using bromothymol blue as the indicator and then diluted with deionized water.
Analysis Procedure:
Measurements were made according to the method described above.
50 μl of sample $S_1$ was injected into a reaction cell, to which an XO-NP mixed enzyme solution was injected to obtain DO consumption ($d_1$). Thereafter 100 μl of sample $S_2$ subjected to an AP pre-reaction was injected thereinto to obtain DO consumption ($d_2$). The K value was determined on the basis of $d_1/d_2 \times 100$.
Results:

Until recently, the freshness of squid was difficult to determine because AdR, not IMP, was formed. However, the method of the present invention makes it possible to determine the K value easily and with good reproducibility and to determine declines in the degree of freshness over two days as shown in the increase in the K value from 44 to 60% in Table 6. The reason for this would appear to be that the crude alkaline phosphatase used in the present invention is mingled with adenosine deaminase (ADA) which carries out the following reaction:

TABLE 6

Evaluation of the Index of Freshness of Squid $$\text{(AdR)} \xrightarrow[H_2O \quad NH_3]{ADA\ (3.5.4.4)} \text{(HxR)}$$

| Days stored | $d_1$ (cm) | $d_2$ (cm) | K value (%) |
|---|---|---|---|
| Half day | 3.45 | 8.08 | 42.7 |
| | 3.55 | 8.20 | 43.3 |
| | 3.88 | 8.19 | 47.4 |
| Average | 3.63 | 8.16 | 44.5 |
| One day | 3.70 | 7.55 | 49.0 |
| | 3.97 | 7.29 | 54.5 |
| | 3.83 | 7.64 | 50.1 |
| Average | 3.83 | 7.49 | 51.2 |
| Two days | 4.60 | 8.22 | 56.0 |
| | 4.90 | 8.00 | 61.3 |
| | 4.96 | 8.08 | 61.4 |
| Average | 4.82 | 8.10 | 59.6 |

EXAMPLE 2

Determination of the K value of Freshly Killed Carp

Figure 11:
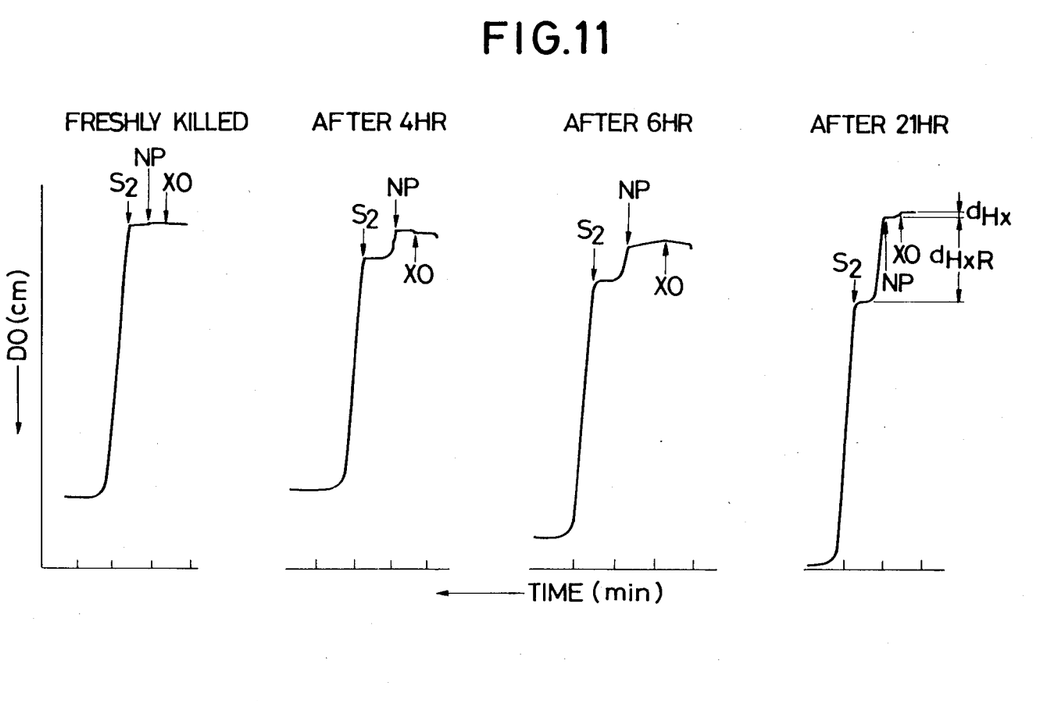
FIG. 11 shows DO consumption curves at time intervals for a freshly killed carp.

Sample:
Pieces of the flesh of three carp of varying sizes were refrigerated and cut at certain time intervals for use.
Preparation of Sample:
Samples extracted with each of PCA and TCA were prepared in the same manner as in Example 1. Methyl orange was used to indicate neutralization.
Analysis Procedure:
Analysis was carried out by injecting 20 μl of sample $S_1$ and 100 μl of an AP-treated sample in the same manner as in Example 1.
Results:
As shown in FIG. 11, no DO consumption was observed in the sample of the large size carp immediately after killing, showing such a high degree of freshness that HxR and Hx are absent, i.e., that the K value = 0. Changes in the K value over time were rather rapid probably because cooling of the samples immediately after killing was insufficient, and because the refrigerator was opened each time a sample was made.

TABLE 7

Evaluation of the Index of Freshness of Carp (K value %)

| Sample | Extractant | 0 hr. | 2 hr. | 4 hr. | 6 hr. | 21 hr. |
|---|---|---|---|---|---|---|
| Large size carp | TCA | 0 | 0 | 2.4 | 8.5 | 30.7 |
| | PCA | 0 | 1.8 | | 9.4 | 26.2 |
| Medium size carp | TCA | 1.9 | 9.2 | 9.1 | 16.7 | 33.0 |
| | PCA | 0 | 3.6 | 8.3 | 12.3 | 42.2 |
| Small size carp | TCA | 3.6 | | 11.0 | 14.3 | 45.6 |
| | PCA | 1.2 | | 4.4 | 16.4 | |

The index of freshness may also be determined by use of an $H_2O_2$ sensor.

The method, in which an XO and NP mixed enzyme solution was added as shown in Example 1, is most convenient for the application of enzymes in obtaining the value of $d_1$ (HxR+Hx) in formula (2).

However, as illustrated in FIGS. 10 and 11, value ($d_{Hx}$) based on the oxidation of hypoxanthine was first obtained by the addition of XO, followed by the addition of NP to obtain value ($d_{HxR}$) based on the conversion of inosine (HxR). Thus $d_1$ was obtained by combining $d_{Hx}$ and $d_{HxR}$ based on formula (5) and, in the same way, $R_{Hx}(\%)$ and $R_{HxR}(\%)$ were obtained, based on formulas (6) and (7).

$$d_1 = d_{Hx} + d_{HxR} \quad (5)$$

$$R_{Hx}(\%) = \frac{d_{Hx} \times 100}{d_2} \quad (6)$$

$$R_{HxR}(\%) = \frac{d_{HxR} \times 100}{d_2} \quad (7)$$

THe values of $R_{Hx}$ and $R_{HxR}$ thus obtained vary with the type of fish or mollusk. Such fish as tuna may be classified as hypoxanthine accumulating when the tendency of $R_{Hx} > R_{HxR}$ is observed, while other fish, such as the carp of Example 2, may be classified as inosine accumulating when the tendency of $R_{HxR} > R_{Hx}$ is observed.

As described above, the present invention makes it possible not only to easily determine the K value but also to estimate more precisely the degree of freshness by comparing $R_{Hx}(\%)$ and $R_{HxR}(\%)$ of the fish in question while also considering the type of fish.

Since detecting time increases by only about 1 minute in the event that the stepwise addition of XO and NP is employed, this method may readily be employed as necessary.

Moreover, the reaction procedure to obtain the value of $d_2$ may be performed by subjecting a divided sample to another reaction cell.

Against this, the reaction procedures as in Examples 1 and 2 reduce the amounts of NP and XO. NP and XO added to determine $d_1$ remain in the reaction cell without losing their activity and can be reused to determine $d_2$ in sample solution $S_2$ which was subjected to prereaction of crude AP. The amount of NP and XO is thus reduced to half. According to the present invention, the reaction cell is fitted with an electrochemical sensor as shown in FIG. 1 and the size of the reaction cell has no connection with the accuracy of the above determination. Even a small reaction cell is adequate and allows the enzyme concentration per unit reaction volume to be raised to carry out rapid reaction and to reduce the amount of enzymes.

As is evident from the above description and Examples, the present invention makes it possible to provide a method for the rapid composition analysis of ATP decomposition products to determine the K value by the application of a DO or $H_2O_2$ measuring instrument which is small, simple and inexpensive, and takes only a few minutes, while the conventional method for determining the K value takes several hours for the composition analysis of ATP decomposition products, and requires analytical instruments such as a liquid chromatograph or an ultraviolet spectrophotometer. The present invention may be widely applied to fish whose degree of freshness is so high that the K value is about 0% and to shellfish and other mollusks such as squid and octopus.

According to the present invention, a very small amount of enzymes can be used for making the compounds to be determined on a DO sensor or $H_2O_2$ sensor.

Further, according to the present invention, the direct calculation of the K value from the DO consumption ratio not only makes manual calculation convenient, but also provides for easy automatic operation by computer. With these advantages, the method for determining the degree of freshness can be readily carried out on site where perishable foodstuffs are produced and sold, as well as in a laboratory with special equipment and skilled personnel. As a result, the method of the present invention can contribute to the food industry, leads to improvements in food sanitation and provides greater protection for consumers, among other benefits.

What is claimed is:

1. A method for determining the index of freshness of fish and mollusks comprising:
   (a) extracting fish or mollusks with a solution of perchloric acid or trichloroacetic acid to produce an extract;
   (b) adding the enzymes: nucleoside phosphorylase and xanthine oxidase, to a portion of the extract;
   (c) electrochemically measuring a value dl from the amount of dissolved oxygen consumed or from the amount of hydrogen peroxide produced due to the combined action of the enzymes;
   (d) adding to another portion of the extract a crude extract containing the enzymes: alkaline phosphate, adenylic acid kinase, AMP deaminase and adenosine deaminase obtained from calf intestine, nucleoside phosphorylase and xanthine oxidase;
   (e) electrochemically measuring a value d2 from the amount of dissolved oxygen consumed or from the amount of hydrogen peroxide produced due to the combined action of the enzymes; and
   (f) determining the index of freshness from the formula K (%)=($d_1/d_2$)×100, wherein K (%) represents the index of freshness, dl represents the combined molar concentrations of inosinde and hypoxanthine in the extract from fish or mollusks, and d2 represents the combined molar concentrations of adensoine-5'-triphosphate, adenosine-5'-diphosphate, adenosine-5'-monophosphate, adenosine, 5'-sodium inosinate, inosine and hypoxanthine in the extract from fish or mollusks.

2. A method, according to claim 1, wherein soldium azide is added to the extract from fish or mollusks to inhibit errors in measurement caused by the presence of catalase in said extract.

* * * * *